United States Patent [19]

Balogh et al.

[11] Patent Number: 4,595,582
[45] Date of Patent: Jun. 17, 1986

[54] DYESTUFF COMPOSITION FOR HISTOLOGICAL EXAMINATIONS

[75] Inventors: Gyorgy Balogh; György Csaba, both of Budapest, Hungary

[73] Assignee: Reanal Finomvegyszergyar, Budapest, Hungary

[21] Appl. No.: 515,924

[22] Filed: Jul. 20, 1983

[63] Continuation-in-part of PCT HU82/00061, Nov. 18, 1982, published as WO83/01779, May 26, 1983

[30] Foreign Application Priority Data

Nov. 20, 1981 [HU] Hungary ............................. 3471/81

[51] Int. Cl.$^3$ ...................... G01N 1/30; G01N 33/48; C09B 67/00
[52] U.S. Cl. .................................... 424/3; 8/94.1 R; 8/94.11; 8/613; 424/7.1
[58] Field of Search ................... 424/3, 7.1; 8/94.1 R, 8/94.11, 613

[56] References Cited

U.S. PATENT DOCUMENTS

| | | | |
|---|---|---|---|
| 3,440,317 | 4/1969 | Martinez | 424/3 |
| 3,906,120 | 9/1975 | Geating | 424/3 |
| 3,916,205 | 10/1975 | Kleinerman | 424/3 |
| 3,928,554 | 12/1975 | Hirshfeld | 424/3 |
| 4,382,075 | 5/1983 | Liao et al. | 424/3 |

FOREIGN PATENT DOCUMENTS 8301779  5/1983  PCT Int'l Appl. ..................... 424/3

OTHER PUBLICATIONS

*Staining Methods Histologic and Histochemical*, Mc-Manus et al., eds., Paul B. Hoeber, Inc., N.Y., 1960, p. 237.

H. J. Conn's Biological Stains, 9th Ed., Lillie, Ed., Williams & Wilkins Co., Baltimore, 1977, pp. 257–266; 328, 385–387; 397–400; 417–421, 428–429; 453–455.

*Primary Examiner*—Christine M. Nucker
*Attorney, Agent, or Firm*—Horst M. Kasper

[57] ABSTRACT

The invention relates to a new dyestuff composition for histological examinations, which comprises
(1) a product formed by the interaction of one molar proportion of one or more thionine dyestuff-sselected from thionine (Colour Index 52,000), toluidine blue (Colour Index 52,040) and dimethyl thionine (Azur A) with at least 0.2 molar proportion of resorcine at elevated temperature,
(2) 0.5 to 2 moles of a dyestuff "A", calculated for one mole of the thionine dyestuff interacted with resorcine, and
(3) 0.5 to 2 moles of a dyestuff "B", calculated for one mole of the thionine dyestuff interacted with resorcine, wherein
dyestuff "A" and dyestuff "B" are alkaline dyestuffs different in colour and pH, and both dyestuff "A" and dyestuff "B" can be mixtures of alkaline dyestuffs similar in colour and pH.

The new dyestuff compositions according to the invention enable one to perform a wide variety of hisotlogical examinations much more quickly, simply and safelyb than before, and can also be applied to detect histological changes which could not be detected before.

19 Claims, No Drawings

DYESTUFF COMPOSITION FOR HISTOLOGICAL EXAMINATIONS

CROSS-REFERENCE TO RELATED APPLICATIONS

This application is a continuation-in-part application of another application filed Nov. 18, 1982 and bearing application Ser. No. PCT/HU82/00061, Nov. 18, 1982, published as WO83/01779, May 26, 1983. This claim is made under Section 35 U.S.C. 365(c), under Section 35 U.S.C. 371 and under any other Section of the U.S.C. supporting such claim.

The invention relates to a new dyestuff composition for histological examinations.

Histological examinations play an essential role in the investigation of pharmaceutically active substances, in biological scientific studies as well as in the therapy. A reliable histopathological diagnosis is an indispensable precondition of the successful treatment of certain diseases and disorders, of which the early recognition of cancerous tissues is of primary importance.

Histological examination methods should give reliable results easy to evaluate. Moreover, the examination methods should be quick, simple and easy to perform, without requiring specific facilities and training.

The histological staining methods known so far do not fulfil these requirements in all respects. The majority of the known staining methods is difficult to perform, time consuming and requires specific attention, and the information supplied is frequently ambiguous. As an example, haematoxylin-eosin test, the most widespread routine method for tissue staining, requires about 90–120 minutes over the freezing and fixing of the section, and the resulting histological picture can be evaluated unambiguously only in the case of striking cytological disorders. Otherwise even an approximate diagnosis, involving the risk of serious errors, can be given only after a professional training of several years, and one should frequently rely on standard reference preparates.

Now it has been found, unexpectedly, that the new dyestuff compositions according to the invention enable one to perform a wide variety of histological examinations much more quickly, simply and safely than before, and the resulting histological picture enables one to set up a much more reliable diagnosis than before even without any dyestuff professional routine or training. Using the new dyestuff compositions according to the invention, histological changes which could not be detected so far by direct staining techniques, or could not be detected at all can be recognized easily and safely.

The invention relates to a new dyestuff composition for histological examinations, which consists of (1) a product formed by the interaction of one molar proportion of one or more thionin dyestuffs selected from thionin (Color Index Generic Name: Biological stain, Color Index 52,000), toluidine blue (Color Index Generic Name: Basic Blue 17, Color Index 52,040) and dimethyl thionin (Azur A Color Index Generic Name: Biological Stain, Color Index Number 52,005) with at least 0.2 molar proportion of resorcinol at elevated temperature, (2) $0.5(M_T/M_A)$ to $2(M_T/M_A)$ moles of a dyestuff "A", calculated for one mole of the thionin dyestuff interacted with resorcinol, and (3) $0.5(M_T/M_B)$ to $2(M_T/M_B)$ moles of a dyestuff "B", calculated for one mole of the thionin dyestuff interacted with resorcinol, wherein dyestuff "A" and dyestuff "B" are alkaline dyestuffs different in color and pH, and both dyestuff "A" and dyestuff "B" can be mixtures of alkaline dyestuffs similar in color and pH, $M_T$ is the molecular weight of the thionin dyestuff, $M_A$ is the molecular weight of dyestuff "A", and $M_B$ is the molecular weight of dyestuff "B", or when any of the thionin dyestuff, dyestuff "A" and dyestuff "B" is a mixture of several substances, $M_T$, $M_A$ and $M_B$ represent the weighted average of the molecular weights of the components of the thionin dyestuff, dyestuff "A" and dyestuff "B", respectively.

Dyestuffs "A" and "B" are preferably different in dispersity as well. When dyestuff "A" or dyestuff "B" is a mixture of dyestuffs, it is preferred to apply dyestuffs with similar dispersities to form the mixture.

The basic component of the dyestuff compositions according to the invention is the product formed by the interaction of a thionin dyestuff with resorcinol at elevated temperature. It has been found that when one mole of a thionin dyestuff is contacted with at least 0.2 moles of resorcinol for a short time at elevated temperatures (preferably at 70°–120° C.), a new substance, different in staining characteristics from the starting thionin dyestuff, is obtained. It has also been observed that when a thionin dyestuff is admixed with resorcinol without heating (e.g. at room temperature), the staining characteristics of the thionin dyestuff do not change. On this basis it is assumed that a chemical interaction takes place between the thionin dyestuff and resorcinol at elevated temperatures; the nature of the product (uniform molecules, a mixture of different reaction products, adduct, complex, etc.) is, however, unknown. It is preferred to utilize 1–5 moles of resorcinol for one mole of thionin dyestuff. Based on our preliminary examinations it is assumed that 3–4 moles of resorcinol are required to obtain a complete interaction with one mole of the thionin dyestuff. The best results are obtained when 3–4 moles of resorcinol are utilized for one mole of the thionin dyestuff; nevertheless the dyestuff composition according to the invention enables one to perform quick and reliable examinations when the thionin dyestuff is present in an excess not greater than 5 moles of thionin dyestuff for one mole of resorcinol. An excess of resorcinol does not disturb staining at all, it is not economical, however, to use resorcinol in excess.

As mentioned above, the thionin dyestuff is contacted with resorcinol at elevated temperatures. The interaction proceeds even at about 50° C., it is preferred, however, to contact these starting substances at higher temperatures, such as at 70°–120° C. The interaction proceeds almost instantaneously; thus e.g. when the starting substances are contacted with each other in an aqueous solution, it is sufficient to boil the solution for some seconds. Any inert liquid capable of dissolving the starting substances can be applied as reaction medium. The term "inert" means here that the liquid does not react with any of the starting substances. The most preferred reaction medium is water.

Dyestuffs "A" and "B" are alkaline background dyestuffs which facilitate the observation of the color effect of the interaction product defined above. As mentioned above, dyestuff "A" may be a single alkaline dyestuff or a mixture of alkaline dyestuffs similar in color, pH, and preferably in dispersity as well; the same holds for dyestuff "B". It is, however, a fundamental requirement that dyestuff "A" (or dyestuff mixture "A") should suffer from dyestuff "B" (or dyestuff mixture "B") in color, pH and preferably in dispersity, too.

Dyestuffs, for which
the difference in light absorption maxima does not exceed $\Delta\lambda = 5$ μm, and
the difference in pH does not exceed 1.0, are regarded as similar, whereas dyestuffs, for which
the difference in light absorption maxima is at least $\Delta\lambda = 10$ μm, and
the difference in pH is at least 2.0, are regarded as different.

From the aspect of the similarity or difference of alkaline dyestuffs, color is the most decisive factor. Thus e.g. when a dyestuff of warm color (red, orange, yellow) or a mixture of such dyestuffs is utilized as dyestuff "A", a dyestuff of cold color (green, blue) or a mixture of such dyestuffs only can be applied as dyestuff "B".

It is preferred to apply e.g. safranin (C.I. Generic Name: Basic red 2, Index 50,240) and/or Pyronin I, also called Pyronin G (C.I. Generic Name: Biological stain, Color Index 45,005) as dyestuff "A", together with e.g. Alcyan blue 8 GX (C.I. Generic Name: Ingrain Blue 1, Color Index 74,240) and/or Licht Grün also called Light Green (C.I. Generic Name: Acid Green 5, Color Index 42,095) as dyestuff "B".

It is preferred to apply the two types of background dyestuffs in a molar ratio of $0.5(M_A/M_B)$ to $2(M_A/M_B)$, wherein $M_A$ and $M_B$ are as defined above. In general, the best results are obtained with dyestuff compositions which contain about $M_T/M_A$ mole of dyestuff "A" and $M_T/M_B$ mole of dyestuff "B" for one mole of the thionin dyestuff interacted with resorcinol.

A particularly preferred dyestuff composition contains 0.3 mole of safranin and 0.3 mole of Alcyan blue for the interaction product of one mole of thionin with 4 moles of resorcinol.

The dyestuff compositions according to the invention can be prepared by methods known per se, such as
(a) the interaction product of the thionin dyestuff and resorcinol, separated in solid form, is admixed with appropriate amounts of dyestuffs "A" and "B", or
(b) appropriate amounts of dyestuffs "A" and "B" are dissolved in the reaction mixture (generally aqueous solution) obtained after the interaction of the thionin dyestuff and resorcinol, and, if desired, the solvent is removed by known techniques, such as distillation, freeze drying, etc.

The dyestuff compositions according to the invention can be applied in histological examinations e.g. for the following purposes:
"normal" staining of nucleus and cytoplasm (for this purpose the haematoxylin-eosin staining discussed above has been applied most frequently,
distinguishing of connective and smooth muscular elements (so far the Mallory or Azan method has been used for this purpose),
staining of mitochondria (this has been done so far e.g. with iron-haematoxylin),
distinguishing of serous and mucinous glands (no direct staining method has been known so far for this purpose; the indirect method is a staining with mucicarmin and a simultaneous background staining),
detection of neurosecretory grains (this has been performed so far e.g. by the Gömöri method),
distinguishing of cartilaginous tissues different in maturity (no appropriate method has been known so far for this purpose), and
determination of the ratio of nuclei active and passive (about to distintegrate, just under disintegration, already disintegrated) from the aspect of protein synthesis (passive nuclei appear in large amounts in tumours, which could not be detected so far by any method).

The known staining methods mentioned above are discussed in detail in the following textbooks: Hans Christian Burck: "Histologische Technik" (Georg Thieme Verlag, Stuttgart, 1969; 2nd edition); A.G.E. Pearse: "Histochemistry, Theoretical and Applied (Little Brown and Co., Boston, 1968).

It is clear from the above that the dyestuff compositions according to the invention have a very wide range of application, and are particularly suitable for this hitopathological diagnostics and examination of cancer.

The invention is elucidated in detail by the aid of the following non-limiting Example.

EXAMPLE 3.0 g of thionin and 1.30 g of resorcinol are dissolved in 1000 ml of water at room temperature (about 25° C.), and the solution is heated to boiling. After 3-5 seconds of boiling the solution is allowed to cool to a bout 25° C., then further 3.80 g of resorcinol are added, and the solution is boiled again for 3-5 seconds. The solution is allowed to cool to room temperature and 2.16 g of Alcyan blue 8 GX are added under stirring. The solution is filtered, the volume of the filtrate is adjusted to 1000 ml with distilled water, and 2.5 g of safranin are dissolved in the mixture. The resulting solution is filtered again, and the volume of the filtrate is adjusted again to 1000 ml with distilled water. This aqueous solution contains 0.003 mole of Alcyan blue 8 GX, 0.003 mole of safranin, and an interaction product formed from 0.01 mole of thionin and 0.04 mole of resorcinol. The solution can be used directly for tissue staining.

If the dyestuff composition is to be stored for a prolonged period, it is subjected to vacuum distillation or freeze drying to remove the solvent. 12.6 g of a powdery dyestuff composition can be obtained from the above solution.

The dyestuff composition can be utilized in histopathological examinations as follows:

The fresh section, obtained e.g. in a surgical intervention, is frozen and then stained for 10 minutes with the above solution. The section is rinsed with tap water for at most one minute, the surroundings of the slide and the section are blotted up with tissue paper, and then the section is treated maximum twice with tert.-butanol for 20 seconds to effect dehydration. Thereafter the section is clarified twice with xylene for one minute, each, and then covered with Canada balm. Thus, the section is ready for histological evaluation within about 25-30 minutes.

Preparates for routine cytological examinations can be made similarly with the difference that fixed sections are used as starting substances.

The various tissue constituents appear in the following colors:
active nuclei: bluish-green
passive nuclei, nuclei before or after disintegration(the number of which is significant in tumorous tissues): red
nucleoli: red conjunctive tissue: blue
smooth muscle: pink
mucinous gland: blue
serous gland: red
mitochondria: violet grains
cartilage: violet, purple, pink, blue or bluish green depending on its maturity
neurosecretory grains: red.

What we claim is:

1. A dyestuff composition for histological examination, which comprises
   (1) a product formed by the interaction of one molar proportion of thionin dyestuff selected from thionin, toluidine blue and dimethyl thionin with a molar proportion of resorcinol from about 0.2 to 5 moles at a temperature of from about 70 degrees centigrade to about 120 degrees centigrade,
   (2) $0.5(M_T/M_A)$ to $2(M_T/M_A)$ moles of a dyestuff "A", and
   (3) $0.5(M_T/M_B)$ to $2(M_T/M_B)$ moles of a dyestuff "B", wherein
   dyestuff "A" and dyestuff "B" are alkaline dyestuffs different in color and pH, both dyestuff "A" and dyestuff "B" can be mixtures of alkaline dyestuffs similar in color and pH,
   $M_T$ is the molecular weight of the thionin dyestuff,
   $M_A$ is the molecular weight of dyestuff "A", and
   $M_B$ is the molecular weight of dyestuff "B", or
   when any of the thionin dyestuff, dyestuff "A" and dyestuff "B" is a mixture of more substances, $M_T$, $M_A$ and $M_B$ represent the weighed average of the molecular weights of the components of the thionin dyestuff, dyestuff "A" and dyestuff "B", respectively.

2. A dyestuff composition as claimed in claim 1, which comprises as component (1) a product formed by the interaction of one mole of a thionin dyestuff with 1 to 5 moles of resorcinol at elevated temperature.

3. A dyestuff composition as claimed in claim 1, which comprises as component (1) a product formed by the interaction of one mole of a histological dyestuff with 3 to 4 moles of resorcinol at elevated temperature.

4. A dyestuff composition as claimed in claim 1, which comprises as dyestuff "A" Alcyan blue 8 GX and as dyestuff "B" safranin.

5. A dyestuff composition as claimed in claim 1, which comprises dyestuffs "A" and "B" in a molar ratio of $0.5(M_A/M_B)$ to $2(M_A/M_B)$, wherein $M_A$ and $M_B$ are as defined in claim 1.

6. A dyestuff composition which comprises the reaction product obtained by the reaction of 1 mole equivalent of thionin dyestuff and 2 to 5 moles of resorcinol carried out at a temperature of 70 to 120 degrees centigrade, 0.2 to 0.4 mole equivalents of alcyan blue and 0.2 to 0.4 mole equivalents of safranin.

7. The dyestuff composition as claimed in claim 6, which comprises 0.3 moles of safranin and 0.3 moles of Alcyan blue calculated for a product formed from the interaction of 1 mole of thionin with 4 moles of resorcinol.

8. The dyestuff composition according to claim 7 wherein the thionin dyestuff comprises thionin.

9. The dyestuff composition according to claim 7 wherein the thionin dyestuff comprises toloudine blue.

10. The dyestuff composition according to claim 7 wherein the thionin dyestuff comprises dimethylthionin.

11. A dyestuff composition for histological examinations comprising a product formed by the interactions of the following components:
    (1) one mole part of a member of the group of thionin dyestuffs consisting of thionin, toluidine blue, dimethyl thionin, and mixtures thereof,
    (2) from about 0.2 to 5 mole parts of resorcinol,
    (3) $0.5(M_T/M_A)$ to $2(M_T/M_A)$ mole parts of a first alkaline dyestuff,
    (4) $0.5(M_T/M_B)$ to $2(M_T/M_B)$ mole parts of a second alkaline dyestuff differing from the first alkaline dyestuff with regard to color and pH;
    wherein the interaction of the components (1) and (2) is performed at a temperature of from about 70 degrees centigrade to about 120 degrees centigrade and wherein the components (3) and (4) are added successively to the interacted composition of components (1) and (2).

12. The dyestuff composition according to claim 10 wherein the interactiom composition of components (1) and (2) is cooled down before the addition of components (3) and (4).

13. The dyestuff composition according to claim 10 wherein the first alkaline dyestuff is a mixture of alkaline dyestuffs similar in color and pH.

14. The dystuff composition according to claim 10 wherein the second alkaline dystuff is a mixture of alkaline dyestuffs similar in color and pH.

15. The dystuff composition according to claim 10 wherein the amount of resorcinol employed is from about 1 to 5 moles.

16. The dystuff composition according to claim 10 wherein the amount of resorcinol employed is from about 3 to 4 moles.

17. The dystuff composition according to claim 10 wherein the amount of first alkaline dyestuff employed is from about 0.5 to 2 moles.

18. The dyestuff composition according to claim 10 wherein the amount of second alkaline dyestuff employed is from about 0.5 to 2 moles.

19. The dystuff compositionaccording to claim 10 wherein the amount of second alkaline dyestuff employed is from about 0.5 to 2 times the number of moles employed of the first alkaline dyestuff.

* * * * *